(12) United States Patent
Wu et al.

(10) Patent No.: US 10,981,164 B2
(45) Date of Patent: *Apr. 20, 2021

(54) CHIP AND APPLICATION THEREOF

(71) Applicant: GeneMind Biosciences Company Limited, Shenzhen (CN)

(72) Inventors: Ping Wu, Shenzhen (CN); Qin Yan, Shenzhen (CN)

(73) Assignee: GENEMIND BIOSCIENCES COMPANY LIMITED, Shenzhen (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/554,372

(22) Filed: Aug. 28, 2019

(65) Prior Publication Data

US 2019/0388888 A1 Dec. 26, 2019

Related U.S. Application Data

(63) Continuation of application No. 15/752,412, filed as application No. PCT/CN2016/095049 on Aug. 12, 2016, now Pat. No. 10,427,154.

(30) Foreign Application Priority Data

Aug. 14, 2015 (CN) .......................... 201510500302.X

(51) Int. Cl.
*B01L 3/00* (2006.01)
*C12M 1/00* (2006.01)
(Continued)

(52) U.S. Cl.
CPC ....... *B01L 3/502707* (2013.01); *B01L 3/5027* (2013.01); *C12M 1/00* (2013.01);
(Continued)

(58) Field of Classification Search
CPC ......... B01L 3/502707; B01L 2200/027; B01L 3/5025; C12Q 1/68; G01N 30/466; B01J 2219/00585

See application file for complete search history.

(56) References Cited

U.S. PATENT DOCUMENTS 6,192,168 B1  2/2001  Feldstein et al.
9,089,843 B2  7/2015  Kim et al.
(Continued)

FOREIGN PATENT DOCUMENTS

CN  102053160 A  5/2011
CN  102411060 A  4/2012
(Continued)

OTHER PUBLICATIONS

Fouad et al "Nanofluidic channels fabricated by e-beam lithograph and polymer reflow sealing", J. Vac. Sci. Tech. B Nov./Dec. 2010, 28(6): 06111-3. (Year: 2010).*

(Continued)

*Primary Examiner* — Betty J Forman
(74) *Attorney, Agent, or Firm* — Seed Intellectual Property Law Group LLP

(57) ABSTRACT

Disclosed is a chip. The chip comprises a substrate (1) and a base layer (2) in pressing arrangement with the substrate; the substrate comprises a first surface (1a) and a second surface (1b) in opposite arrangement, reaction tank arrays formed by a plurality of flowing channels (11) are arranged on the first surface of the substrate at intervals, two oppositely arranged side walls (111, 112) of each flowing channel (11) stretch along the length direction of the flowing channel (11) and intersect at two ends of the flowing channel to form two tapered tail ends (113) with included angles, and a fluid inlet hole (12) and a fluid outlet hole (13) which are communicated with the second surface of the substrate are respectively provided on the surfaces of the two tapered tail (Continued)

ends (113); and the base layer (2) comprises a transparent base (21) and a spacing layer (22) arranged on the surface of the transparent base, the spacing layer (22) is in contact with the firs surface (1a) of the substrate, and a corrosion groove is provided on the spacing layer (22) corresponding to a position where the flowing channel (11) is located. The flow field distribution of the chip is good, the deformation rate of a base in the chip is low, and the fluid in the chip can be fully flushed or replaced. Also disclosed is an application of the chip.

15 Claims, 3 Drawing Sheets

(51) Int. Cl.
*C12M 1/34* (2006.01)
*C12Q 1/68* (2018.01)
*C12Q 1/6837* (2018.01)

(52) U.S. Cl.
CPC .................. *C12M 1/34* (2013.01); *C12Q 1/68* (2013.01); *C12Q 1/6837* (2013.01); *B01L 2200/027* (2013.01); *B01L 2200/10* (2013.01); *B01L 2200/12* (2013.01); *B01L 2300/0816* (2013.01); *B01L 2300/0877* (2013.01); *B01L 2300/166* (2013.01)

(56) References Cited

U.S. PATENT DOCUMENTS

| | | | |
|---|---|---|---|
| 10,427,154 B2* | 10/2019 | Wu | ........................ B01L 3/5027 |
| 2004/0037739 A1* | 2/2004 | McNeely | ................ B01L 9/527 |
| | | | 422/417 |
| 2005/0229696 A1 | 10/2005 | Takayama | |
| 2015/0176070 A1 | 6/2015 | Ota et al. | |
| 2015/0301033 A1* | 10/2015 | Guo | ..................... C12Q 1/6834 |
| | | | 506/9 |
| 2016/0167049 A1 | 6/2016 | Narahara et al. | |

FOREIGN PATENT DOCUMENTS

| | | |
|---|---|---|
| CN | 103008035 A | 4/2013 |
| CN | 103350982 A | 10/2013 |
| CN | 103611584 A | 3/2014 |
| CN | 104428656 A | 3/2015 |
| CN | 104627953 A | 5/2015 |
| CN | 105112290 A | 12/2015 |
| CN | 105154323 A | 12/2015 |
| CN | 204874530 U | 12/2015 |
| EP | 1 643 249 A1 | 4/2006 |
| EP | 2659977 A1 | 11/2013 |
| WO | 2015050998 A2 | 4/2015 |

OTHER PUBLICATIONS

Backhouse et al "DNA sequencing in a monolithic microchannel device", Electrophoresis 21, 150-156, 2000.

* cited by examiner

CHIP AND APPLICATION THEREOF

The present disclosure is a continuation of U.S. application Ser. No. 15/752,412, filed Feb. 13, 2018, which is a U.S. national stage application of PCT/CN2016/095049, filed Aug. 12, 2016, which claims priority to a prior application No. 201510500302.X entitled "Single-Molecule Sequencing Chip" filed with the Patent Office of China on Aug. 14, 2015, the contents of which are incorporated herein by reference.

FIELD

The present disclosure relates to the technical field of DNA detection chips, and in particular to a chip and application thereof.

BACKGROUND

Since the beginning of the 21st century, the completion of the human genome project has had a huge impact on contemporary biological research and medical research. In terms of gene sequence analysis, the emphasis in the post-genome era has been transferred from whole genome sequencing of individual species to comparison of individual genetic differences and genetic differences between species in the level of genome DNA sequences of a species. Target gene resequencing will be the mainstream technology of clinical gene detection in the future. Honored as the third-generation sequencing technology, single-molecule sequencing technology has the distinguishing feature of directly identifying DNA fragments with high fidelity, and has higher detection sensitivity than high-throughput sequencing technology (collectively referred to as the second-generation sequencing technology) because it can identify single nucleic acid molecules.

Chips are key components to achieve the sequencing technology. The second-generation sequencing chips are the mainstream products on the market at present, and for most of them, a high-density nano array is obtained by using semiconductor nano processing technology, which is fine and complex with a very high cost, and needs to be accomplished using large high-precision instruments and clean rooms of ultrahigh levels. In addition, in order to achieve the purpose of high-throughput sequencing, the second-generation sequencing chip usually has a large chip channel width, and usually has the problems of non-uniform distribution of fluid flow field and easy deformation tendency of cover glasses during biochemical reaction by way of sample injection under negative imbibition pressure. The problem of non-uniform flow field distribution will cause incomplete reagent replacing, and affect the biochemical reaction. Cover glass deformation will affect the chip quality, and will further affect the acquisition of basic optical signals.

Single molecule sequencing technology neither has high requirements for the sequencing data size, nor needs an ultrahigh density nano array like the second-generation sequencing chip, so that the traditional second-generation sequencing chip has been unable to match with the single-molecule sequencing technology. Therefore, it is necessary to provide a chip suitable for single molecule sequencing.

SUMMARY

In view of this, the present disclosure provides a chip and an application thereof. The flow field distribution of the chip is good, the deformation rate of the chip is low, and the fluid can be fully flushed or replaced.

In a first aspect, the present disclosure provides a chip, which includes a substrate and a base layer in press with the substrate; wherein the substrate comprises a first surface and a second surface which are arranged oppositely, an array formed by multiple channels being arranged on the first surface of the substrate at intervals, two oppositely arranged side walls of each of the channels stretching along the longitudinal direction of the channel and intersecting at two ends of the channel to form two tapered tail ends with included angles, and an inlet hole and an outlet hole connected with the second surface of the substrate being respectively provided on the two tapered tail ends; and the base layer comprises a transparent layer and a spacing layer arranged on the surface of the transparent layer, the spacing layer being in contact with the first surface of the substrate, and grooves being provided on the spacing layer corresponding to the positions where the channels are located.

In an embodiment of the present disclosure, the array includes 15 to 25 channels.

In an embodiment of the present disclosure, the width of the spacing layer along a direction perpendicular to the longitudinal direction of the channel is 1 to 1.5 mm.

As described in the present disclosure, the spacing between adjacent channels is 1 to 1.5 mm.

In an embodiment of the present disclosure, the included angle at the tapered tail end is 30° to 60°.

In an embodiment of the present disclosure, the distance between intersections of the two oppositely arranged side walls of each of the channels is the length of each channel, and the length of each of the channels is 50 to 75 mm.

In an embodiment of the present disclosure, the distance between the two oppositely arranged side walls of each of the channels is the width of each channel, and the width of each of the channels is 1 to 2 mm.

In an embodiment of the present disclosure, the depth of each of the channels is 0.6 to 1 mm.

The depth of the channel is preferably 0.6 to 1 mm. According to the hydrodynamic resistance law of rectangular channels, when a channel is doubled in the thickness direction, the flow resistance is reduced to $\frac{1}{8}$ of the original one. Small flow resistance contributes to fluid flow, and facilitates biochemical reaction of fluid in the channel.

Furthermore, in an embodiment of the present disclosure, each of the channels has a length of 50 mm, a width of 1 mm, and a depth of 0.6 mm.

In terms of fluid, a channel with a narrower width is more advantageous to the flushing and replacing between fluid, and the longitudinal section at both ends of the channel is designed as a triangle. When fluid flows through the channel, there is no backflow phenomenon in the channels.

In an embodiment of the present disclosure, the substrate has a first side length perpendicular to the longitudinal direction of the channels, and the distance from each of the intersections of the two oppositely arranged side walls of each of the channels to the first side length of the substrate is 0.5 to 1 cm.

In an embodiment of the present disclosure, the inlet hole and the outlet hole are coaxial.

In an embodiment of the present disclosure, the diameter of the inlet hole is 300 to 500 μm.

In an embodiment of the present disclosure, the diameter of the outlet hole is 300 to 500 μm.

As described in the disclosure, an array of the single-molecule sequencing chip formed by multiple channels is arranged on the first surface of the substrate at intervals, and inlet holes and outlet holes are formed on the surfaces of the two tapered tail ends of each of the channels for fluid inflow and outflow.

As described in the present disclosure, the inlet holes and outlet holes are used to connect to fluid input and output devices. For example, pipette tips, pipe joints, etc. can be respectively inserted into the fluid inlet holes and fluid outlet holes, so as to disperse fluid input and output points of each channel, and input/output fluid to/from each channel without interference.

In an embodiment of the present disclosure, the material of the substrate includes, but is not limited to, one or more of polydimethylsiloxane (PDMS), polymethyl methacrylate (PMMA), ethylene-vinyl acetate (EVA) and polyurethane (PUA), as long as casting process can be implemented.

In an embodiment of the present disclosure, the transparent layer includes transparent glass, quartz or an organic polymer material with one of the functional groups of an epoxy group, an amino group, a carboxyl, a sulfydryl and an aldehyde group on the surface.

Furthermore, in an embodiment of the present disclosure, the transparent layer is transparent glass or quartz with an epoxy group on the surface.

In an embodiment of the present disclosure, the material of the spacing layer is polymethylglutarimide (PMGI). The spacing layer is used to block contact between samples in each channel and guarantee separate control of the samples in each of the channels.

The spacing layer is obtained through washing off a part of a complete protection layer provided on the surface of the transparent layer in contact with each of the channels using a corrodent. In an embodiment of the present disclosure, the material of the protection layer is polymethylglutarimide.

In an embodiment of the present disclosure, the spacing layer is obtained through injecting a reagent into each channel to wash off the polymethylglutarimide layer on the transparent layer in contact with each of the channels, so that the functional groups (epoxy group, amino group, carboxyl, sulfydryl, aldehyde group, etc.) on the surface of the transparent layer are exposed. The spacing layer is used to block contact between samples in each of the channels and guarantee separate control of the samples in each of the channels.

In an embodiment of the present disclosure, the depth of the corrosion groove is 1 to 5 μm.

In the embodiments of the present disclosure, the chip further includes a probe immobilized on the surface of the transparent layer of the chip, and the surface of the transparent layer is modified to have one or more of epoxy group, amino group, carboxyl, sulfydryl and aldehyde group.

The functional groups (e.g., epoxy group, amino group, carboxyl, sulfydryl and aldehyde group) on the surface of the transparent layer can react with the functional groups (e.g. carboxyl, phosphate, amino group, etc.) of the probe, so that the probe is immobilized on the transparent layer of the chip, and subsequently the chip is applied to the target area capture, nucleic acid sequencing, and other fields. For example, the epoxy group on the transparent layer can have chemical reaction with the DNA probe modified with —$NH_2$, and the probe is immobilized through a new bond of —$CH_2$—NH— to the surface of the layer modified with an epoxy group.

The probe can include a primer (preferably a targeting primer). The primer can be a nucleic acid for target or random capture of nucleic acid of samples to be tested.

In a second aspect, the present disclosure provides the application of the chip as described in the first aspect in sequence capture and/or nucleic acid sequencing. The nucleic acid sequencing includes DNA and/or RNA sequencing.

Unless otherwise specified, the "targeting primer" and "sequence", "primer" or "probe" mentioned herein are interchangeable, and refer to a fragment of nucleotide sequence (oligonucleotide).

The sequence capture can include primer (preferably targeting primer) immobilization and capturing target nucleic acid to be tested or known as the "target area capture" (also referred to as "template nucleic acid" in the technical field of nucleic acid sequencing) using the immobilized primer. The "complex of primer-nucleic acid to be tested", the same as the "complex of primer/nucleic acid to be tested", means a complex formed by connection between a primer and a nucleic acid to be tested. Unless otherwise specified, the "nucleic acid to be tested" and "template nucleic acid" described in the present disclosure are interchangeable.

When the chip is applied in the field of sequencing, a fluorescence detector can be provided outside the transparent layer. The fluorescence detector is one of a charge coupled device (CCD) or a complementary metal oxide semiconductor (CMOS). Through biochemical reaction in microfluidic channels, a variety of optical wavelengths can be used to detect a base at a specific location of a DNA molecule immobilized on a transparent layer, so as to determine the DNA sequence immobilized on the transparent layer.

The chip provided in the present disclosure has a certain number of channels, each of which has tapered tail ends with included angles, so that there is no backflow phenomenon in the channel, so the fluid flow field distribution in the channel is far better than that of the second-generation sequencing chip, meanwhile the integrated design of a plurality of channels increases the supporting points of the base, which makes the base deformation problem almost negligible. The single-molecule sequencing chip can realize separate control of samples in each of the channels, thus guarantee no cross contamination between samples, and also simplify subsequent data processing. In addition, unlike the second-generation sequencing chip, the single-molecule sequencing chip does not need to add a specific fragment of "barcode" before injection of each sample, so as to identify each sample from biological information analysis after sequencing.

The preparation method of the chip provided in the present disclosure includes the following steps: (1) preparing an anode membrane of an array on the surface of a base plate by photolithography according to a designed graphic template of the array; (2) casting the anode membrane with a model glue; curing it at 90-100° C. for 1 to 3 h after vacuum degassing the same to transfer the anode membrane of the array to the bottom of the model glue; removing the membrane to obtain a model glue layer with multiple channels; and drilling a hole at each of the two ends of each of the channels to form an inlet hole and an outlet hole, thereby to obtain a substrate; (3) modifying a base layer by the step of: preparing a protection layer on the surface of a transparent base to obtain the transparent layer with the modified surface; (4) encapsulating a chip: after oxygen plasma cleaning of the substrate and the transparent layer with the modified surface, pressing the substrate with the transparent layer to form a space for accommodating fluid; then injecting a corrodent into each of the channels, to wash off a part of the protection layer in contact with each of the channels, thereby to obtain a spacing layer on the surface of the transparent layer, thus completing preparation of the chip.

In this application, the spacing layer is obtained through washing off a part of the protection layer in contact with each of the channels using a corrodent. In an embodiment of the present disclosure, the material of the protection layer is polymethylglutarimide; and the material of the spacing layer is polymethylglutarimide.

According to an embodiment of the present disclosure, the chip is prepared using the following method: (1) preparing an anode membrane of an array on the surface of a base plate by photolithography according to a designed graphic template of the array; (2) casting the anode membrane with a model glue; curing it at 90-100° C. for 1-3 h after vacuum degassing the same to transfer the anode membrane of the array to the bottom of the model glue; removing the membrane to obtain a model glue layer with a plurality of channels; and drilling a hole at each of the two ends of each of the channels to form an inlet hole and an outlet hole, thereby obtaining a substrate; (3) modifying a base by the step of preparing a polymethylglutarimide (PMGI) layer on the surface of a transparent base to obtain the transparent layer with the modified surface; (4) encapsulating a chip: after oxygen plasma cleaning of the substrate and the transparent layer with the modified surface, pressing the substrate with the transparent layer to form a space for accommodating fluid; and then injecting N-methylpyrrolidone (NMP for short) into each of the channels and waiting for 10 min-15 min, to wash off the polymethylglutarimide layer in contact with each of the channels, thereby to obtain a spacing layer on the surface of the transparent layer, thus completing preparation of the chip.

In this application, the chip comprises a substrate and a base layer in press with the substrate; the substrate comprises a first surface and a second surface which are arranged oppositely, an array formed by multiple channels being arranged on the first surface of the substrate at intervals, two oppositely arranged side walls of each of the channels stretching along the longitudinal direction of the flow channel and intersecting at two ends of the flow channel to form two tapered tail ends with included angles, and an inlet hole and an outlet hole connected with the second surface of the substrate being respectively provided on the two tapered tail ends; and the base layer comprises a transparent layer and a spacing layer arranged on the surface of the transparent layer, the spacing layer being in contact with the first surface of the substrate, and grooves being provided on the spacing layer corresponding to positions where the channels are located.

In an embodiment of the present disclosure, in step (3), the transparent layer includes transparent glass, quartz or an organic polymer material with one of the functional groups of an epoxy group, an amino group, a carboxyl, a sulfydryl and an aldehyde group on the surface.

In an embodiment of the present disclosure, in step (1), the base plate includes one of silicon wafer, glass, metal or ceramic.

In an embodiment of the present disclosure, in step (2), the model glue includes, but is not limited to, one or more of polydimethylsiloxane (PDMS), polymethyl methacrylate (PMMA), ethylene-vinyl acetate (EVA) and polyurethane (PUA), as long as the model glue is applicable to soft lithography.

Furthermore, in an embodiment of the present disclosure, in step (2), the model glue is polydimethylsiloxane (PDMS).

As described in the present disclosure, the material of the substrate is the same as that of the model glue.

In an embodiment of the present disclosure, in step (3), the thickness of the polymethylglutarimide (PMGI) layer is 1 to 5 μm.

In the present disclosure, the full name of PMGI in English is polymethylglutarimide (PMGI), which is purchased from MicroChem Company, and the product name is one or more of SF1, SF2, SF3, SF4, SF5, SF6, SF7, SF7.5, SF8, SF9, SF10, SF11, SF12, SF13, SF14, SF15, SF17, SF19 and SF23.

In an embodiment of the present disclosure, the PMGI is polymethylglutarimide with the product name of SF11 purchased from MicroChem Company.

In an embodiment of the present disclosure, in step (4), the injection volume of N-methylpyrrolidone in each channel is 100 to 500 μL.

The injection volume of the N-methylpyrrolidone allows to corrode polymethylglutarimide on the transparent layer in contact with each of the channels, and obtain grooves on the spacing layer corresponding to the positions where the channels are located, so that the functional groups (epoxy group, amino group, carboxyl, sulfydryl, aldehyde group, etc.) carried on the upper surface of the transparent layer are exposed. The spacing layer is used to block contact between samples in each of the channels and guarantee separate control of samples in each of the channels.

As described in the present disclosure, before oxygen plasma treatment of the surface of the substrate and the transparent layer with the modified surface, a PMGI layer is prepared to protect the functional groups (one of the epoxy group, amino group, carboxyl, sulfydryl, aldehyde group, etc.) on the surface of the transparent layer, and prevent them from being affected by oxygen plasma treatment, so that subsequent samples are immobilized on the transparent layer. After oxygen plasma cleaning of modified transparent layer, the hydrophobic surface of the transparent layer becomes hydrophilic. N-methylpyrrolidone is then injected into each of the channels, wherein N-methylpyrrolidone can corrode the PMGI in contact with each of the channels, so that the functional groups on the surface of the transparent layer are exposed again.

The channels of the single-molecule sequencing chip are hydrophilic, so the chip can reduce non-specific adsorption of gene samples (e.g. DNA) to be tested and at the same time bring no effect to the functional groups on the surface of the base.

In an embodiment of the present disclosure, in step (4), the press of the substrate with the transparent layer specifically includes the following steps: preliminarily fitting the substrate with the transparent layer, pressing them with a heavy object in an oven at 95 to 120° C., and then baking them for 1 to 3 h.

In an embodiment of the present disclosure, in step (1), the photolithography includes the following steps: a. preparing a negative photoresist on the surface of a base plate by spin coating to get a base plate with uniform glue, wherein the thickness of the photoresist layer on the surface of the base plate is 600 to 650 μm;

b. prebaking the base plate with uniform glue, wherein the prebaking temperature is controlled as follows: slowly heating the base plate to 90 to 100° C., keeping it at the temperature for 15 to 20 min, and then naturally cooling it down to room temperature;

c. with the designed graphic template of the array as a mask, covering the surface of the prebaked base plate with the mask for exposure for 90 to 150 s;

d. postbaking the exposed base plate, wherein the postbaking temperature is controlled as follows: firstly slowly heating the base plate to 90 to 95° C., keeping it at the temperature for 5 to 10 min, and then naturally cooling it down to room temperature; and e. immersing the postbaked base plate in a developing solution for development, and washing off the part except for the mask to obtain the anode membrane of the array.

In an embodiment of the present disclosure, before step a of the photolithography, the method further includes the following pretreating steps of the base plate: washing the surface of the base plate using anhydrous ethanol and water successively, and then heating the cleaned base plate on a hot plate at 150° C. for 10 min to fully evaporate the moisture on the surface.

In an embodiment of the present disclosure, after step e of the photolithography, the method further includes the following steps: f hard baking the anode membrane of the array obtained from step e. The so-called hard baking is realized by the following steps: placing a glass plate on the anode membrane and then placing an iron block thereon; heating the anode membrane and the glass plate as well as the iron block to 130 to 150° C. to bake the same for 45 to 60 min.

The hard baking aims to more firmly adhere the photoresist layer of the anode membrane to the surface of the base plate and to increase the etching resistance of the photoresist layer.

In an embodiment of the present disclosure, in step b, the prebaking temperature is controlled as follows: firstly baking the base plate with uniform glue at 65° C. for 6 min, gradually heating them up to 95° C. at a rate of 1° C./min and keeping them at the temperature for 20 min, and then naturally cooling them down to room temperature. The prebaking step aims to evaporate the organic solvent in the photoresist and to cure the photoresist.

In an embodiment of the present disclosure, in step d, the postbaking temperature is controlled as follows: firstly gradually heating the exposed base plate up to 95° C. at a rate of 0.5° C./min, keeping them at the temperature for 5 min, and then naturally cooling them down to room temperature at a rate of 1 to 3° C./min. The postbaking step aims to realize full crosslinking reaction of the exposed negative photoresist.

In an embodiment of the present disclosure, the negative photoresist is SU-8 2150.

In a third aspect, the present disclosure provides a kit, including the chip and reagent described in the first aspect of the present disclosure. The reagents to be used may be chosen according to the application of the kit.

In a fourth aspect, the present disclosure provides the application of the kit described in the third aspect in sequence capture and/or nucleic acid sequencing. The nucleic acid sequencing includes DNA and/or RNA sequencing.

The reagents to be used may be selected according to the application of the kit, and may include one or more reagents. For example, when the chip is used for nucleic acid sequencing (e.g., single molecule sequencing), the required reagents can include immobilization reaction reagent, extension reaction reagent, imaging reagent and reagent for exciding molecular markers for optical detection.

It is understandable that the kit further includes a buffer solution or other reagents required for sequencing. In the embodiments of the present disclosure, none of the immobilization reaction reagent, extension reaction reagent, imaging reagent and reagent for exciding molecular markers for optical detection is specially limited. The existing commonly used reagents in this field are usable. For example, those skilled in the art may respectively prepare buffer solutions in different processes in view of the immobilization reaction reagent, extension reaction reagent, imaging reagent, reagent for exciding molecular markers for optical detection, etc. as required.

In a fifth aspect, the present disclosure provides a process for obtaining a target area, including the following steps: combining the nucleic acid to be tested with the probe on the chip of the present disclosure, so as to hybridize the target area to the chip, wherein the probe is connected to the surface of the transparent layer of the chip.

In an embodiment of the present disclosure, a process for obtaining a target area includes: immobilizing a probe to the surface of the transparent layer of the chip in any one of the foregoing embodiments of the present disclosure; adding nucleic acids of one or more samples to be tested into the channels of the chip, so that the target area is hybridized to the probe, thereby to obtain the target area.

In a sixth aspect, the present disclosure provides a process for nucleic acid sequence determination, including the following steps: (i) hybridizing a template nucleic acid with a first optical detection marker at the ends with the probe on the chip in any one of the foregoing embodiments to obtain a first complex, wherein the probe is bond to the surface of the base layer; (ii) imaging the first complex to obtain a first image; (iii) mixing the first complex, polymerase and one or more of nucleotides with a second optical detection marker, and adding one or more nucleotides with a second optical detection marker by polymerase reaction to the first complex to obtain an extension product, wherein the nucleotide with the second optical detection marker includes a cleavable group and a nucleotide; (iv) imaging the extension product to obtain a second image; (v) removing the cleavable group from the extension product to obtain a second complex; (vi) replacing the first complex with the second complex, and repeating the above steps (ii) to (v) once or more times to determine the nucleotide of the template.

The beneficial effects of the present disclosure include the following aspects:

1. The chip has a certain number of channels, each of which is designed as a narrow channel, and both the fluid inlet and outlet are designed to be tapered, which is beneficial to form a fluid buffer zone, so that the fluid in the flow channel is fully flushed and replaced without a fluid backflow area, thus facilitating biochemical reaction; at the same time, the depth of the channels is larger, so the flow resistance of the fluid in the channels is smaller, which can improve the property of the chip.

2. Integrated design of a plurality of channels in the chip increases the supporting surface of the substrate, which is beneficial to reduce substrate/base layer deformation caused by negative imbibition pressure, and overcomes the problems of abnormal fluid sample injection and poor image acquisition effect in the chip system caused by base deformation.

3. The chip adopts the design of a plurality of parallel channels independent of each other, which can make the samples in each of the channels be controlled separately and thus ensure no cross contamination between the samples. Unlike current second-generation sequencing chip, the chip, if used for single-molecule sequencing, does not need to add a specific fragment of "barcode" sequence before injection of each sample to identify each sample, so the chip can simplify the sample preparation process and the subsequent biological information analysis process.

4. Due to its superstrong hydrophobicity, the model glue (such as PDMS, etc.) is easy to nonspecifically adhere to biological macromolecules such as DNA, so that it is seldom reported to be applied to the substrate of a DNA sequencing chip. In the present disclosure, the chip suitable for single molecule DNA sequencing is prepared based on soft lithography-casting process, hydrophobic substrate surface is changed to hydrophilic one by plasma treatment on the premise of protecting functional groups on the surface of the base, so that it can meet the requirements of the DNA sequencing chip. The channels of the chip not only can reduce nonspecific adsorption of DNA molecules to be tested, but also enable the functional groups on the surface of the substrate not to be affected.

5. The anode membrane of the array made by photolithography can be casted and used repeatedly, which is advantageous to batch production of the single molecule sequencing chip, and will further reduce the manufacturing cost.

DETAILED DESCRIPTION

Preferred embodiments of the present disclosure are described below. It should be noted that for those skilled in the art, some improvements and modifications can also be made without departing from the principle of the present disclosure. These improvements and modifications are also regarded as within the scope of protection of the present disclosure.

Embodiment 1

Figure 1:
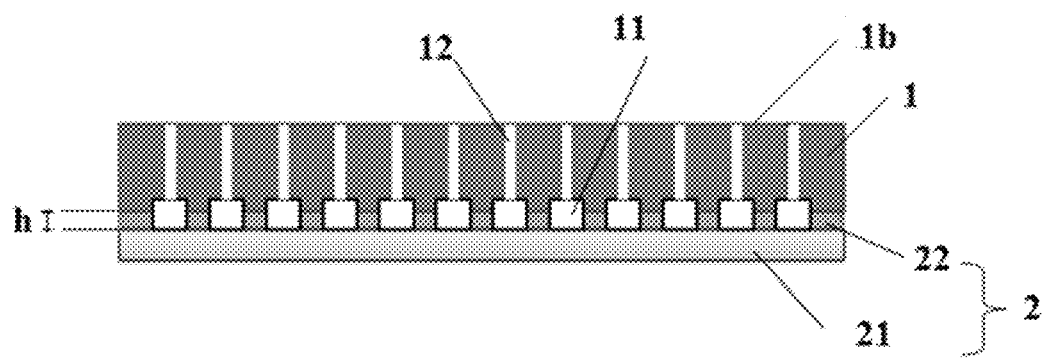
FIG. 1 is a schematic diagram of a sectional structure of a single molecule sequencing chip in accordance with embodiment 1 of the present disclosure, wherein the numeral 1 represents a substrate, 21 represents a transparent layer, 22 represents a spacing layer on the transparent layer 21, 2 represents a base layer composed of 21 and 22, 1b represents a second surface of the substrate 1, 11 represents a channel, 12 represents an inlet hole connected with the second surface 1b of the substrate, and the depth of grooves on the spacing layer 22 corresponding to the positions where the channels are located is denoted by h.
Figure 2:
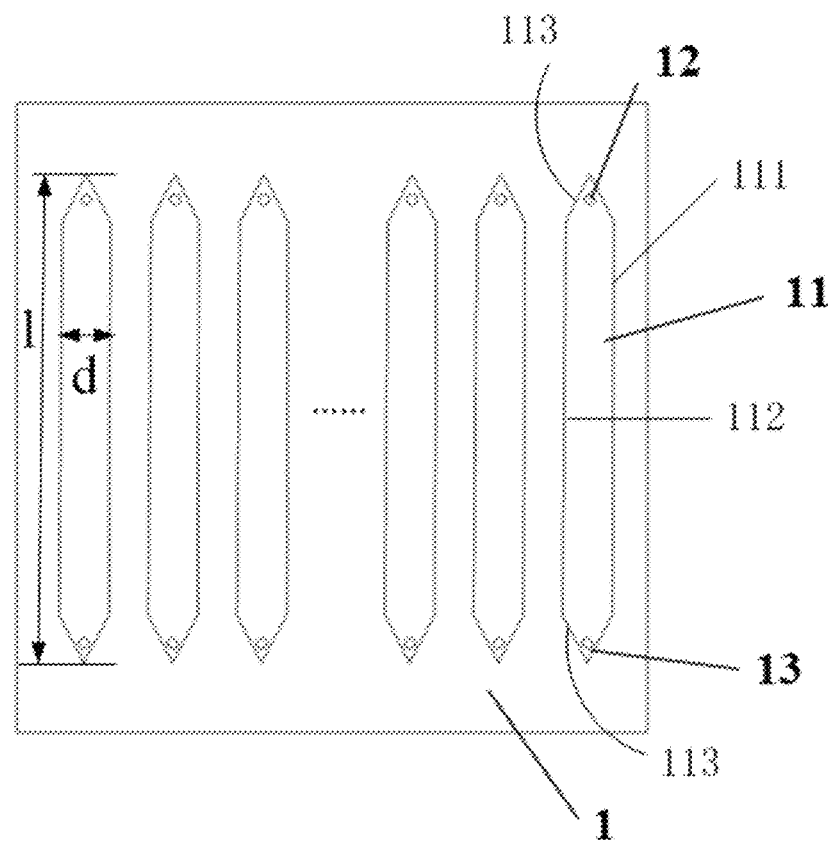
FIG. 2 is a schematic structure diagram of a top view of a single molecule sequencing chip in embodiment 1 of the present disclosure, wherein numeral 1 represents a substrate, 11 represents a channel, 12 and 13 represent an inlet hole and an outlet hole respectively, 111 and 112 represent two oppositely arranged side walls of the channel respectively, 113 represents a tapered tail end of the flow channel, the distance denoted by d is the width of each channel, and the distance denoted by l is the length of each channel.
Figure 3:
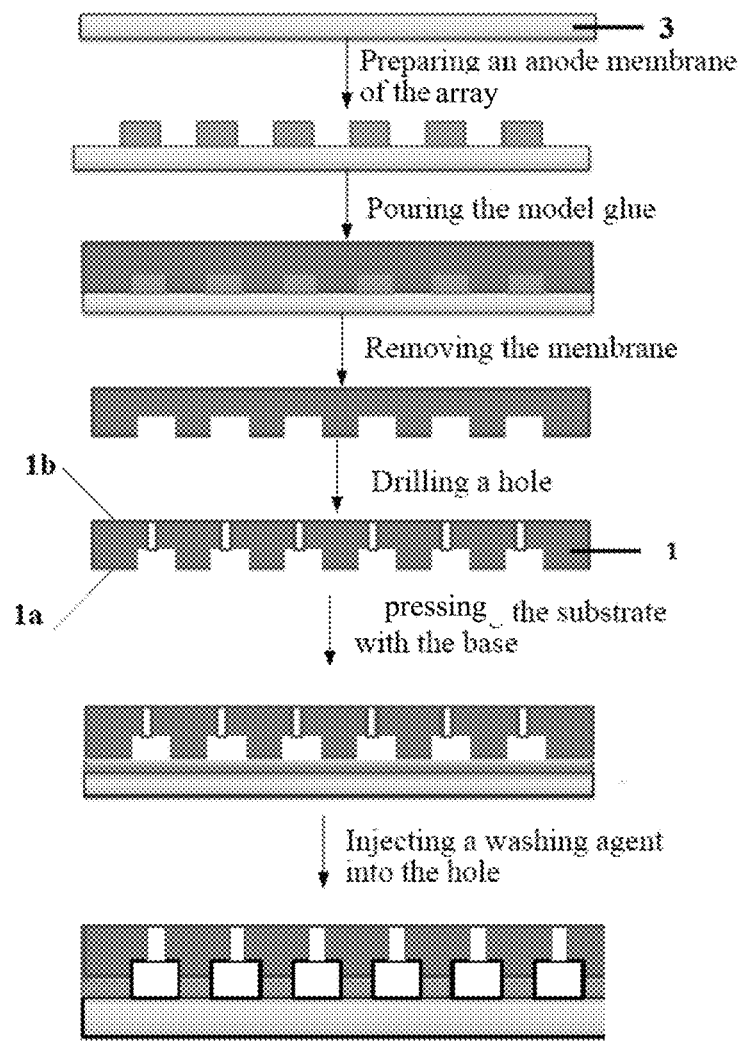
FIG. 3 is a schematic diagram of a preparation method of a single molecule sequencing chip in the embodiment of the present disclosure, wherein numeral 3 represents a base for preparing an anode membrane of an array, 1a represents a first surface of a substrate 1, and 1b represents a second surface of the substrate 1.

A schematic diagram of a structure of a single molecule sequencing chip in this example is shown in FIG. 1. As can be seen from FIG. 1 and FIG. 2 which is a schematic structure diagram of a top view of a substrate, the single molecule sequencing chip includes a substrate 1 and a base layer 2 in press with the substrate, the substrate 1 including a first surface (not shown in FIG. 1, denoted by 1a in FIG. 3) and a second surface 1b which are oppositely arranged, an array formed by a plurality of channels 11 being arranged on the first surface of the substrate at intervals, two oppositely arranged side walls 111 and 112 of each of the channels 11 stretching along the longitudinal direction of the channel 11 and intersecting at two ends of the channel to form two tapered tail ends 113 with included angles, and an inlet hole 12 and an outlet hole 13 connected with the second surface 1b of the substrate being respectively provided on the two tapered tail ends 113; and the base layer 2 includes a transparent layer 21 and a spacing layer 22 arranged on the surface of the transparent layer 21, the spacing layer 22 being in contact with the first surface of the substrate, grooves being provided on the spacing layer 11 corresponding to the positions where the channels are located, and the depth of the grooves being denoted by h.

As can be seen from FIG. 1, there is still a residual polymethylglutarimide (PMGI) layer on the transparent layer 21, but the PMGI layer on the corresponding transparent layer in contact with the channels has been fully removed, i.e. the spacing layer 22 arranged on the transparent layer 21 at intervals is obtained. The spacing layer 22 is formed by washing off the PMGI layer on the transparent layer in contact with the channels through injecting a washing agent into each of the channels, so that the epoxy group carried on the upper surface of the transparent layer is exposed. The spacing layer 22 is used to block contact between samples in the channels and guarantee separate control of samples in the respective channels. The depth of the grooves on the spacing layer corresponding to the positions where the channels are located is 1 μm.

In this embodiment, the included angle of the tapered tail end 113 is 60°.

In this embodiment, the array includes 20 channels, the spacing between adjacent channels is 1 mm, and the width of the spacing layer 22 along a direction perpendicular to the longitudinal direction of the flow channel is 1 mm. The distance between the intersections of two oppositely arranged side walls of each of the channels is the length of each channel, and is denoted by l in FIG. 2. The distance between the two oppositely arranged side walls of each of the channels is the width of each channel, and is denoted by d in FIG. 2.

In this embodiment, the length l of each channel is 50 mm.

In this embodiment, the width w of each channel is 1 mm.

In this embodiment, the depth d of each channel is 0.6 mm.

In this embodiment, the substrate has a first side length perpendicular to the longitudinal direction of the flow channel, and the distance from each intersection of two oppositely arranged side walls of each of the channels to the first side length of the substrate is 0.5 cm.

In this embodiment, the inlet hole 12 and the outlet hole 13 are coaxial.

In this embodiment, the diameter of the inlet hole 12 and the outlet hole 13 is 300 μm.

In this embodiment, the transparent layer 21 is transparent borosilicate glass with an epoxy group on the surface. The material of the spacing layer is PMGI, and the depth of the corrosion groove is 1 μm.

In this embodiment, the material of the substrate 1 is polydimethylsiloxane (PDMS). The preparation method of the single molecule sequencing chip in this embodiment (see the schematic diagram of the preparation method in FIG. 3) includes the following steps: (1) preparing an anode membrane of an array on the surface of the silicon wafer which is used as a base plate, by photolithography according to a designed graphic template of the array, specifically including the following steps: a. washing the surface of the silicon wafer as the base plate with anhydrous ethanol and water successively, and then heating the cleaned silicon wafer on a hot plate at 150° C. for 10 min to fully evaporate the moisture on the surface; placing the treated silicon wafer onto a rotating objective table of a spin coater for spin coating of negative photoresist SU-8 2150, and starting the spin coater to uniformly spread the photoresist on the silicon wafer and thereby to obtain the silicon wafer with uniform glue, wherein the thickness of the photoresist layer on the surface of the silicon wafer is 600 μm, the acceleration time of the spin coater is set as 18 s, the time of uniformly spin coating is set as 60 s, and the rotation speed during uniformly spin coating is 1000 rpm; b. prebaking the silicon wafer with uniform glue, wherein the prebaking temperature is controlled as follows: firstly baking the silicon wafer at 65° C. for 6 min, gradually heating it to 95° C. at a rate of 1° C./min, keeping it at the temperature for 20 min, and then naturally cooling it down to room temperature; c. with the designed graphic template of the array as a mask, covering the surface of the prebaked silicon wafer with the mask for exposure for 120 s; d. postbaking the exposed silicon wafer with the postbaking temperature controlled as follows: firstly gradually heating the silicon wafer to 95° C. at a rate of 0.5° C./min, keeping it at the temperature for 5 min, and then naturally cooling it down to room temperature at a rate of 2° C./min; e. immersing the postbaked silicon wafer in a developing solution SU-8 for development, washing off the part except for the mask, washing off residual developing solution with isopropanol, and finally washing off residual isopropanol with deionized water to obtain the anode membrane of the array; f hard baking the anode membrane of the array obtained from step e, so that the photoresist layer of the anode membrane is more firmly adhered to the surface of the silicon wafer, wherein the so-called hard baking is realized by the following steps: placing a glass plate on the anode membrane and placing an iron block thereon; heating the anode membrane and the glass plate as well as the iron block to 150° C. to bake the same at the temperature for 60 min; and naturally cooling them down to room temperature, thereby obtaining the hard baked anode membrane of the array, the anode membrane being convex; (2) mixing glue A and glue B of polydimethylsiloxane (PDMS) of Dow Chemical Company at a mass ratio of 10:1 while fully stirring, pouring the mixture into a glass dish with the above-mentioned anode membrane of the array placed therein in advance, vacuumizing the glass dish in a vacuum device for 1 h, keeping the glass dish in a drying oven with the bottom surface kept horizontal after bubbles are fully vacuumized, and curing the mixture at 95° C. for 1 h, so that the anode membrane of the array is transferred to the bottom of the model glue; taking out the glass dish from the drying oven, cooling the glass dish, cutting away the pattern part within the cured model glue with a knife, removing the membrane to obtain a model glue layer with grooves of a plurality of channels, and drilling a hole at each of the two ends of the bottom of each flow channel to form a fluid inlet hole and a fluid outlet hole, thereby to obtain a substrate; (3) modifying a base layer by the step of: preparing a polymethylglutarimide (PMGI, a product of SF11 series of MicroChem Company) layer on the surface of transparent borosilicate glass, which is used as the transparent layer and has an epoxy group on the surface, to obtain the transparent layer with the modified surface, wherein the PMGI layer is 1 μm thick; (4) encapsulating a chip: cleaning the substrate and the transparent layer with the modified surface using an oxygen plasma cleaning machine, then pressing the substrate with the transparent layer to form a space for accommodating fluid; then injecting 100 μL of N-methylpyrrolidone (NMP for short) into each channel and waiting for 10 min, to wash off the PMGI layer in contact with the channels and expose an epoxy group carried on the surface of the borosilicate glass, thereby to obtain a spacing layer on the surface of the transparent layer, respectively inserting pipe joints into the inlet hole and outlet hole at the two ends of each of the channels, and sealing and gluing the same with resin, thus completing preparation of the single-molecule sequencing chip.

Figure 4:
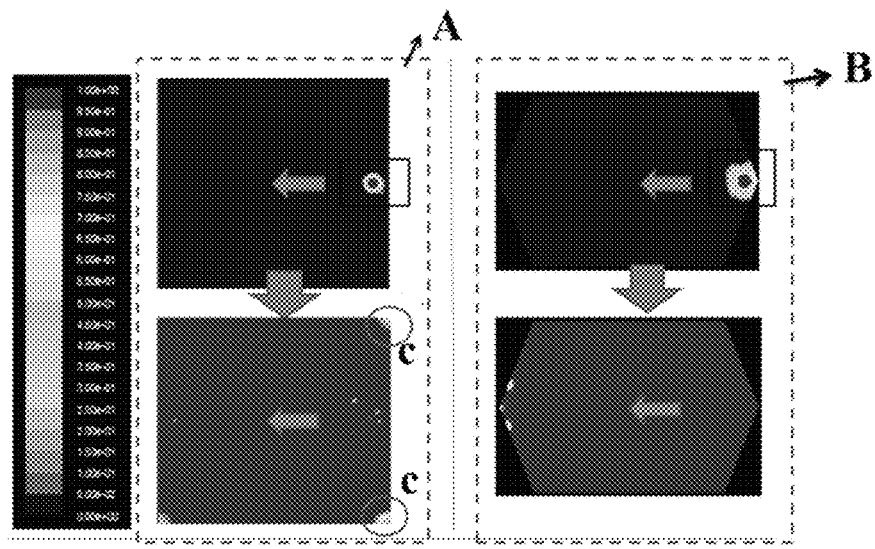
FIG. 4 shows the comparison of the hydrodynamic simulation results of a two-generation sequencing chip and a single molecule sequencing chip in embodiment 1 of the present disclosure.

The hydrodynamic simulation results of the single-molecule sequencing chip prepared in embodiment 1 are shown in FIG. 4, wherein A is a flow field of the single molecule sequencing chip without tapered design at both ends of the channel, and B is a flow field of the single molecule sequencing chip with a tapered entrance segment. The color data bar in the left column of FIG. 4 shows the volume fraction of fluid (blue at the bottom, and red on the top). Blue denotes air initially existing in the chip, and red denotes fluid about to enter the chip. The fluid flows from right to left, and enters from one point (Red points in A and B indicate the initial flow state, and are respectively circled with a box. The channel gradually changes from blue to red over time. When the channel fully becomes red, it means that the whole channel has been full of the fluid). As can be obviously seen from FIG. 4, the fluid backflow area c represented by a circle is almost absent in B with a tapered design.

The above comparison shows that both the inlet and outlet of the single molecule sequencing chip prepared in the present disclosure are designed to be tapered, which is beneficial to form a fluid buffer zone, so that the fluid in the flow channel is fully flushed and replaced without a fluid backflow area, and facilitates biochemical reaction.

Embodiment 2

A single molecule sequencing chip comprises a substrate and a base layer in press with the substrate; the substrate comprises a first surface and a second surface which are arranged oppositely, an array formed by multiple channels being arranged on the first surface of the substrate at intervals, two oppositely arranged side walls of each of the channels stretching along the longitudinal direction of the channel and intersecting at two ends of the channel to form two tapered tail ends with included angles, and an inlet hole and an outlet hole connected with the second surface of the substrate being respectively provided on the two tapered tail ends; and the base layer comprises a transparent layer and a spacing layer arranged on the surface of the transparent layer, the spacing layer being in contact with the first surface of the substrate, and grooves being provided on the spacing layer corresponding to the positions where the channels are located.

In the embodiment 2, the included angle of the tapered tail end is 30°, the array includes 25 channels, and the spacing between adjacent channels is 1.2 mm. The length of each channel is 75 mm, the width of each channel is 1.5 mm, and the depth d of each channel is 0.8 mm. The substrate has a first side length perpendicular to the longitudinal direction of the channel, and the distance from each intersection of two oppositely arranged side walls of each channel to the first side length of the substrate is 0.8 cm. The inlet hole and the outlet hole are coaxial, and the diameter of them is 400 µm. In this example, the transparent layer is transparent borosilicate glass with an epoxy group on the surface. The material of the substrate is polydimethylsiloxane (PDMS). The material of the spacing layer is PMGI, and the depth of the groove on the spacing layer corresponding to a position where the flow channel is located is 3 µm.

The preparation method of the single molecule sequencing chip in the embodiment 2 includes the following steps: (1) preparing an anode membrane of an array on the surface of a silicon wafer which is used as a base plate, by photolithography according to the designed graphic template of the array, specifically including the following steps; a. washing the surface of the silicon wafer as the base plate using anhydrous ethanol and water successively, and then heating the cleaned silicon wafer on a hot plate at 150° C. for 10 min to fully evaporate the moisture on the surface; placing the treated silicon wafer onto a rotating objective table of a spin coater for spin coating of negative photoresist SU-8 2150, and starting the spin coater to uniformly spread the photoresist on the silicon wafer, to thereby obtain the silicon wafer with uniform glue, wherein the thickness of the photoresist layer on the surface of the silicon wafer is 650 µm, the acceleration time of the spin coater is set as 18 s, the time of uniformly spin coating is set as 60 s, and the rotation speed during uniformly spin coating is 1000 rpm; b. prebaking the silicon wafer with uniform glue, wherein the prebaking temperature is controlled as follows: slowly heating the silicon wafer to 100° C., keeping it at the temperature for 15 min, and then naturally cooling it down to room temperature; c. with the designed graphic template of the array as a mask, covering the surface of the prebaked silicon wafer with the mask for exposure for 150 s;

d. postbaking the exposed silicon wafer with the temperature controlled as follows: firstly slowly heating the silicon wafer to 90° C., keeping it at the temperature for 10 min, and then naturally cooling it down to room temperature; e. immersing the postbaked silicon wafer in a developing solution SU-8 for development, washing off the part except for the mask, washing off residual developing solution with isopropanol, and finally washing off residual isopropanol with deionized water to obtain the anode membrane of the array; f hard baking the anode membrane of the array obtained from step e, so that the photoresist layer of the anode membrane is more firmly adhered to the surface of the silicon wafer, wherein the so-called hard baking is realized by the following steps: placing a glass plate on the anode membrane and placing an iron block thereon; heating the anode membrane and the glass plate as well as the iron block to 130° C. to bake the same at the temperature for 45 min; and naturally cooling them down to room temperature to obtain hard baked anode membrane of the array, the anode membrane being convex; (2) casting the anode membrane using a model glue PDMS, and curing it at 90° C. for 3 h after vacuum degassing the same to transfer the anode membrane of the array to the bottom of the model glue, removing the membrane to obtain a model glue layer with multiple channels, and drilling a hole at each of the two ends of each of the channels to form an inlet hole and an outlet hole, thereby to obtain a substrate; (3) modifying a base layer by the step of: preparing a PMGI layer on the surface of transparent borosilicate glass, which is used as the transparent layer and has an epoxy group on the surface, to obtain the transparent layer with the modified surface, wherein the PMGI layer is 3 µm thick; (4) encapsulating a chip: after cleaning the substrate and the transparent layer with the modified surface using an oxygen plasma cleaning machine, taking them out, preliminarily fitting the substrate with the transparent layer, baking them in an oven at 120° C. with a heavy object thereon for 2 h, thus completing press fit of the substrate with the transparent layer, and thereby forming a space for accommodating fluid; then injecting 300 µL of NMP into each of the channels and waiting for 12 min, to wash off a PMGI layer in contact with the channels and expose an epoxy group carried on the surface of the borosilicate glass, thereby to obtain a spacing layer on the surface of the transparent layer, respectively inserting pipe joints into the inlet hole and outlet hole at the two ends of each of the channels, and sealing and gluing the same with resin, thus obtaining the single-molecule sequencing chip.

Embodiment 3

A single molecule sequencing chip comprises a substrate and a base layer in press with the substrate; the substrate comprises a first surface and a second surface which are arranged oppositely, a array formed by a plurality of channels being arranged on the first surface of the substrate at intervals, two oppositely arranged side walls of each of the channels stretching along the longitudinal direction of the channel and intersecting at two ends of the channel to form two tapered tail ends with included angles, and an inlet hole and an outlet hole connected with the second surface of the substrate being respectively provided on the two tapered tail ends; and the base layer comprises a transparent layer and a spacing layer arranged on the surface of the transparent layer, the spacing layer being in contact with the first surface of the substrate, and grooves being provided on the spacing layer corresponding to the positions where the channels are located.

In the embodiment 3, the included angle of the tapered tail end is 45°, the array includes 7 channels, and the spacing between adjacent channels is 1.5 mm, i.e. the width of the spacing layer along a direction perpendicular to the longitudinal direction of the channel is 1.5 mm. The length of each channel is 60 mm, the width of each channel is 2 mm, and the depth d of each channel is 1 mm. The substrate has a first side length perpendicular to the longitudinal direction of the channel, and the distance from each intersection of two oppositely arranged side walls of each channel to the first side length of the substrate is 1 cm. The inlet hole and the outlet hole are coaxial, and the diameter of them is 500 µm.

In the embodiment 3, the transparent layer is transparent borosilicate glass with an epoxy group. The material of the spacing layer is PMGI, and the depth of the groove is 5 µm. The material of the substrate is polydimethylsiloxane (PDMS).

The preparation method of the single molecule sequencing chip in the embodiment 3 includes the following steps: (1) preparing an anode membrane of a array on the surface of a piece of glass which is used as a base plate, by photolithography according to a designed graphic template of the array, specifically including the following steps: a. washing the surface of the piece of glass as the base plate using anhydrous ethanol and water successively, and then heating the cleaned base plate on a hot plate at 150° C. for 10 min to fully evaporate the moisture on the surface; placing the treated base plate onto a rotating objective table of a spin coater for spin coating of negative photoresist SU-8 2150, and starting the spin coater to uniformly spread the photoresist on the silicon wafer, thereby to obtain the base plate with uniform glue, wherein the thickness of the photoresist layer on the surface of the base plate is 620 μm, the acceleration time of the spin coater is set as 18 s, the time of uniformly spin coating is set as 60 s, and the rotation speed during uniformly spin coating is 1000 rpm; b. prebaking the base plate with uniform glue, wherein the prebaking temperature is controlled as follows: slowly heating the silicon wafer to 95° C., keeping it at the temperature for 18 min, and then naturally cooling it down to room temperature; c. with the designed graphic template of the array as a mask, covering the surface of the prebaked silicon wafer with the mask for exposure for 150 s; d. postbaking the exposed base plate with the temperature controlled as follows: firstly slowly heating the silicon wafer to 92° C., keeping it at the temperature for 8 min, and then naturally cooling it down to room temperature; e. immersing the postbaked silicon wafer in a developing solution SU-8 for development, washing off the part except for the mask, washing off residual developing solution with isopropanol, and finally washing off residual isopropanol with deionized water to obtain the anode membrane of the array; f hard baking the anode membrane of the array obtained from step e, so that the photoresist layer of the anode membrane is more firmly adhered to the surface of the base plate, wherein the so-called hard baking is realized by the following steps: placing a glass plate on the anode membrane and then placing an iron block thereon; heating the anode membrane and the glass plate as well as the iron block to 140° C. to bake the same at the temperature for 50 min; and naturally cooling them down to room temperature to obtain hard baked anode membrane of the array, the anode membrane being convex; (2) casting the anode membrane using a model glue PDMS, and curing it at 100° C. for 2 h after vacuum degassing the same to transfer the anode membrane of the array to the bottom of the model glue, removing the membrane to obtain a model glue layer with grooves of a plurality of channels, and drilling a hole at each of the two ends of each of the channels to form an inlet hole and an outlet hole, thereby to obtain a substrate; (3) modifying a base layer by the step of: preparing a PMGI layer on the surface of transparent borosilicate glass, which is used as the transparent layer and has an epoxy group on the surface, to obtain the transparent layer with the modified surface, wherein the PMGI layer is 5 μm thick; (4) encapsulating a chip: after cleaning the substrate and the transparent layer with the modified surface using an oxygen plasma cleaning machine, taking them out, preliminarily fitting the substrate with the transparent layer, baking them in an oven at a temperature of 95° C. with a heavy object thereon for 1 h, thus completing press fit of the substrate with the transparent layer, and thereby forming a space for accommodating fluid; then injecting 500 μL of NMP into each of the channels and waiting for 15 min, to wash off a PMGI layer in contact with the channels and expose an epoxy group carried on the surface of the borosilicate glass, thereby to obtain a spacing layer on the surface of the transparent layer, respectively inserting pipe joints into the inlet hole and outlet hole at both ends of each of the channels, and sealing and gluing the same with resin to obtain the single-molecule sequencing chip, which includes a substrate and a base layer in press fit with the substrate, the base layer including a transparent layer and a spacing layer arranged on the surface of the transparent layer.

Figure 5:
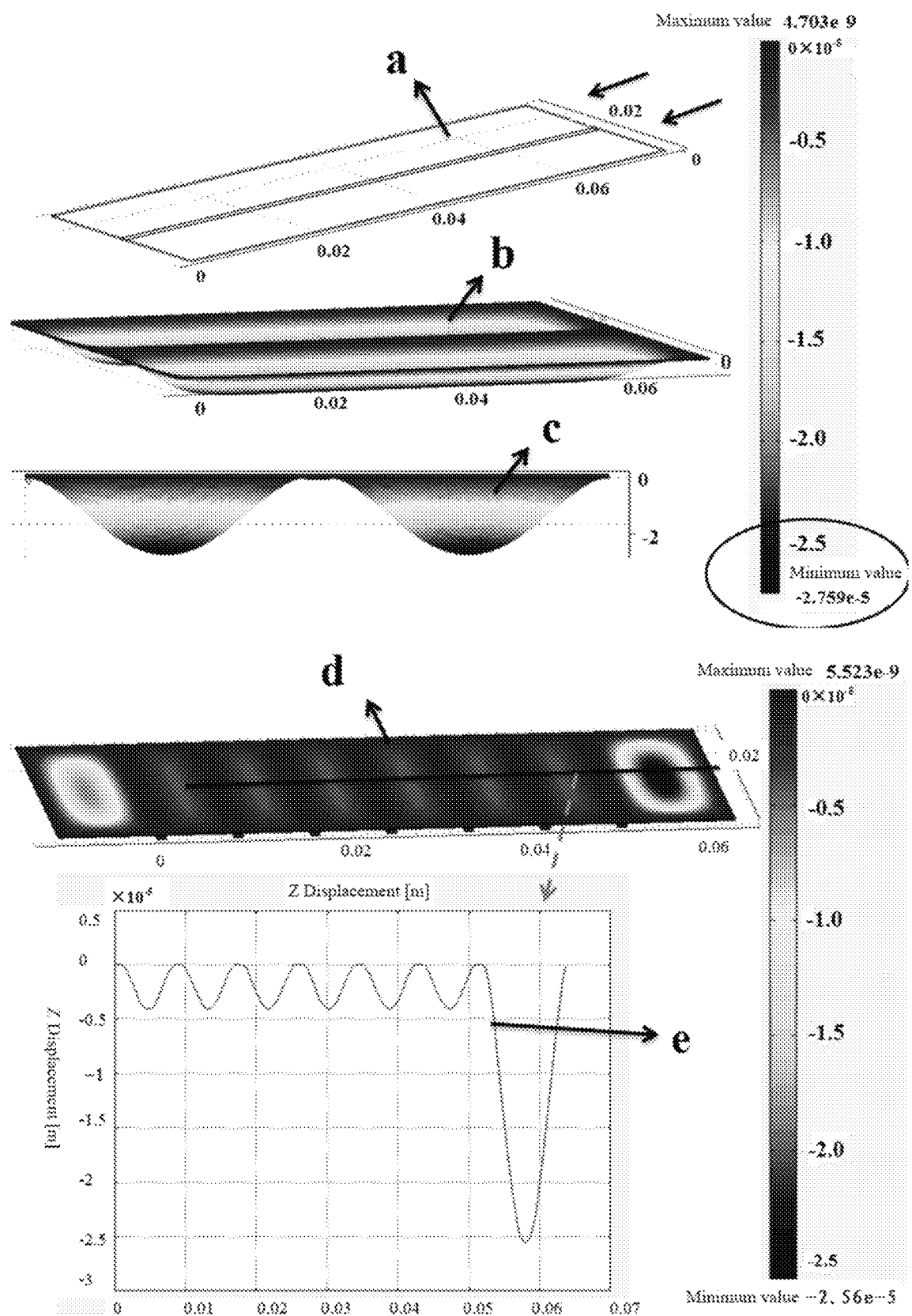
FIG. 5 shows the comparison of transparent layer deformation of a two-generation sequencing chip and a single molecule sequencing chip in embodiment 3 of the present disclosure.

Most of second-generation sequencers and single molecule sequencers achieve reagent sample injection by negative imbibition pressure using an injection pump. Because a chip usually uses very thin glass (150-170 μm) as a base layer during bonding, the total line pressure drop will subject the internal and external surfaces of the glass base to certain pressure difference, which will lead to certain deformation of the glass base layer. The deformation not only strongly affects normal sample injection of the reagents in the whole flow path system, but also affects the image acquisition effect of the chip. In order to highlight the technical effect of the present disclosure, in the present disclosure, the deformation of the glass substrate/ base layer of the common second-generation sequencing chip (with two channels) and that of the chip (with 7 channels) of embodiment 3 under the same negative pressure are compared, and the same negative pressure (15 kpa) is applied to the two chips. Supposing the mechanical parameters of the glass base layer are consistent (Young modulus: 72.9 kN/mm$^2$, poisson ratio: 0.2, density: 2150 g/cm$^3$), the results are as shown in FIG. 5: a represents a typical second-generation chip model (with one support in the middle, and two channels), b indicates the deformation of the glass base at a typical flow rate of 10 μL/s i.e. under a pressure of 15 kpa, and c is a side view of the deformation thereof; and d represents a chip model with 6 supporting surfaces only (with 7 channels), and e indicates the deformation quantity of the base of a chip with 7 channels (embodiment 3). The color bar represents a deformation quantity, with the bottom being blue, the top being red, and the unit being m, wherein the negative sign represents downward deformation.

As can be seen from FIG. 5, because the width of the channel of the second-generation sequencer is large (about 5 to 10 mm), the deformation quantity reaches nearly 28 μm under a line pressure drop of 15 kpa. For the chip in this embodiment 3, when 6 supporting solid surfaces are arranged (forming 7 channels), the deformation quantity of the glass base is less than 5 μm under the same pressure of 15 kpa. Predictably, when the number of channels of the chip is increased to 15 to 25, the deformation quantity of the base of the chip will be reduced to a smaller value. In addition, by calculation, the flow resistance of the chip in the embodiment 3 is very small, and substantially will not reach the line pressure drop of 15 kpa. In fact, the overall line pressure drop of the chip will not exceed 5 kpa.

Embodiment 4

A single molecule sequencing chip comprises a substrate and a base layer in press with the substrate; the substrate comprises a first surface and a second surface which are arranged oppositely, a array formed by a plurality of channels being arranged on the first surface of the substrate at intervals, two oppositely arranged side walls of each of the channels stretching along the longitudinal direction of the channel and intersecting at two ends of the channel to form two tapered tail ends with included angles, and an inlet hole and an outlet hole connected with the second surface of the substrate being respectively provided on the two tapered tail ends; and the base layer comprises a transparent layer and a spacing layer arranged on the surface of the transparent layer, the spacing layer being in contact with the first surface of the substrate, and grooves being provided on the spacing layer corresponding to the positions where the channels are located.

In this embodiment 4, the included angle of the tapered tail end is 60°, the array includes 15 channels, and the spacing between adjacent channels is 1 mm, i.e. the width of the spacing layer along a direction perpendicular to the longitudinal direction of the channel is 1.5 mm. The length of each channel is 50 mm, the width of each channel is 1 mm, and the depth d of each channel is 0.6 mm. The substrate has a first side length perpendicular to the longitudinal direction of the channel, and the distance from each intersection of two oppositely arranged side walls of each channel to the first side length of the substrate is 0.6 cm. The inlet hole and the outlet hole are coaxial, and the diameter of them is 300 µm.

In this embodiment 4, the transparent layer is quartz with an aldehyde group on the surface. The material of the spacing layer is PMGI, and the depth of the groove is 3 µm. The material of the substrate is PMMA. The DNA molecule modified with —NH$_2$ to be tested can react with the aldehyde group on the transparent layer of the chip of the embodiment, and is therefore fixed.

The preparation method of the single molecule sequencing chip in the embodiment 4 includes the following steps: (1) preparing an anode membrane of a array on the surface of a silicon wafer which is used as a base plate, by photolithography according to a designed graphic template of the array; a. washing the surface of the silicon wafer as the base plate using anhydrous ethanol and water successively, and then heating the cleaned silicon wafer on a hot plate at 150° C. for 10 min to fully evaporate the moisture on the surface; placing the treated silicon wafer onto a rotating objective table of a spin coater for spin coating of negative photoresist SU-8 2150, and starting the spin coater to uniformly spread the photoresist on the silicon wafer, thereby to obtain the silicon wafer with uniform glue, wherein the thickness of the photoresist layer on the surface of the silicon wafer is 650 µm, the acceleration time of the spin coater is set as 18 s, the time of uniformly spin coating is set as 60 s, and the rotation speed during uniformly spin coating is 1000 rpm; b. prebaking the silicon wafer with uniform glue, wherein the prebaking temperature is controlled as follows: slowly heating the silicon wafer to 100° C., keeping it at the temperature for 15 min, and then naturally cooling it down to room temperature; c. with the designed graphic template of the array as a mask, covering the surface of the prebaked silicon wafer with the mask for exposure for 150 s; d. postbaking the exposed silicon wafer with the temperature controlled as follows: firstly gradually heating the silicon wafer to 95° C. at a rate of 0.5° C./min, keeping it at the temperature for 5 min, and then naturally cooling it down to room temperature at a rate of 1° C./min; e. immersing the postbaked silicon wafer in a developing solution SU-8 for development, washing off the part except for the mask, washing off residual developing solution with isopropanol, and finally washing off residual isopropanol with deionized water to obtain the anode membrane of the array, wherein the anode membrane is convex; (2) casting the anode membrane using polymethyl methacrylate (PMMA) as a model glue; curing it at 95° C. for 1 h after vacuum degassing the same to transfer the anode membrane of the array to the bottom of the model glue; removing the membrane to obtain a model glue layer with a plurality of channels; and drilling a hole at each of the two ends of each of the channels to form an inlet hole and an outlet hole, to thereby obtain a substrate; (3) modifying a base layer by the step of: preparing a PMGI layer on the surface of quartz, which is used as the transparent layer and has an aldehyde group on the surface, to obtain the transparent layer with the modified surface, wherein the PMGI layer is 3 µm thick; (4) encapsulating a chip: after cleaning the substrate and the transparent layer with the modified surface using an oxygen plasma cleaning machine, taking them out, preliminarily fitting the substrate with the transparent layer, baking them in an oven at 100° C. with a heavy object thereon for 3 h to thus completing press of the substrate with the base layer, and thereby forming a space for accommodating fluid; then injecting 300 µL of NMP into each channel and waiting for 10 min, to wash off a PMGI layer in contact with the channels, thereby to obtain a spacing layer on the surface of the transparent layer, thus completing preparation of the single-molecule sequencing chip, wherein the single-molecule sequencing chip comprises a substrate and a base layer in press with the substrate, and the base layer comprises a transparent layer and a spacing layer arranged on the surface of the transparent layer.

The above embodiments are only a few embodiments of the present disclosure, and are specifically described in detail, but cannot be understood to limit the scope of this disclosure. It should be noted that for those of ordinary skill in the art, a number of modifications and improvements can also be made without departing from the concept of the present disclosure, and all these modifications and improvements fall within the scope of protection of the present disclosure.

What is claimed is:
1. A chip, comprising:
 a substrate comprising a first surface, a second surface arranged opposite the first surface of the substrate, and an array including a plurality of channels in the first surface of the substrate at intervals, side walls of each channel of the plurality of channels being oppositely arranged and stretching along a longitudinal direction of a respective channel and intersecting at two ends of the respective channel to form two tapered tail ends, an inlet hole and an outlet hole connected with the second surface being respectively provided on the two tapered tail ends; and
 a base layer in contact with the substrate, the base layer comprising a transparent layer and a spacing layer arranged on a portion of a surface of the transparent layer between each of the channels, the spacing layer being a portion of the side walls of each channel of the plurality of channels, the spacing layer being in contact with the first surface of the substrate.

2. A chip according to claim 1, wherein the array includes 15 to 25 channels.

3. A chip according to claim 1, wherein a width of the spacing layer in a direction perpendicular to the longitudinal direction of the respective channel is 1 to 1.5 millimeters (mm).

4. A chip according to claim 1, wherein a width of each channel of the plurality of channels is 1 to 2 mm, the width of each channel being a distance between the side walls of each channel of the plurality of channels.

5. A chip according to claim 1, wherein a depth of each channel of the plurality of channels is 0.6 to 1 mm.

6. A chip according to claim 1, wherein a length of each channel of the plurality of channels is 50 to 75 mm, the length of each channel being a distance between intersections of the two oppositely arranged side walls of each channel of the plurality of channels.

7. A chip according to claim 1, wherein a diameter of the inlet hole is 300 to 500 micrometers (μm), and a diameter of the outlet hole is 300 to 500 μm.

8. A chip according to claim 1, wherein the tapered tail ends have included angles of 30° to 60°.

9. A chip according to claim 1, wherein the substrate comprises a material comprising polydimethylsiloxane, polymethyl methacrylate, ethylene-vinyl acetate, polyurethane, or a combination thereof.

10. A chip according to claim 1, wherein the spacing layer comprises polymethylglutarimide.

11. A chip according to claim 1, wherein the spacing layer has grooves corresponding to positions where the channels are located.

12. A chip according to claim 11, wherein a depth of each groove is 1 to 5 μm.

13. A chip according to claim 1, further comprising a probe immobilized on the surface of the transparent layer of the chip, wherein the surface of the transparent layer is modified to have one or more of epoxy group, amino group, carboxyl, sulfydryl and aldehyde group.

14. A method of nucleic acid capture and/or nucleic acid sequencing, the method comprising:
adding a sample comprising a nucleic acid into a channel of the plurality of channels of the chip according to claim 1; and
imaging at least a portion of the chip.

15. A kit, comprising the chip according to claim 1; and one or more reagents for nucleic acid sequencing.

* * * * *